United States Patent [19]

Yung

[11] Patent Number: 4,726,237

[45] Date of Patent: Feb. 23, 1988

[54] FLUID METERING APPARATUS AND METHOD

[75] Inventor: Ching Yung, Monte Sereno, Calif.

[73] Assignee: Sequoia-Turner Corporation, Mountain View, Calif.

[21] Appl. No.: 746,988

[22] Filed: Jun. 19, 1985

[51] Int. Cl.[4] ............................................. G01N 1/10
[52] U.S. Cl. ............................. 73/864.83; 73/863.73
[58] Field of Search ........... 73/863.01, 863.71, 863.72, 73/863.73, 864.83

[56] References Cited

U.S. PATENT DOCUMENTS

| | | | |
|---|---|---|---|
| 1,605,832 | 11/1926 | Garhart . | |
| 2,453,553 | 11/1948 | Tansley | 225/26 |
| 2,846,121 | 8/1958 | Ronnebech | 222/133 |
| 2,857,082 | 10/1958 | Perkins | 222/255 |
| 2,858,851 | 11/1958 | Holl | 137/625.18 |
| 2,904,070 | 9/1959 | Lynott | 137/552.5 |
| 3,100,984 | 8/1963 | Martin | 73/23 |
| 3,122,168 | 2/1963 | Wright | 137/625.48 |
| 3,131,706 | 5/1964 | Harban | 137/15 |
| 3,160,015 | 12/1964 | Carlton . | |
| 3,222,135 | 12/1965 | Ashmead | 23/253 |
| 3,549,994 | 12/1970 | Rothermel et al. | 324/71 |
| 3,567,389 | 3/1971 | Coulter et al. | 23/253 |
| 3,567,390 | 3/1971 | Rothermel | 23/253 |
| 3,583,232 | 6/1971 | Isreeli | 73/522 GC |
| 3,652,228 | 3/1972 | Bernard | 23/253 R |
| 3,858,450 | 1/1975 | Jones | 73/863.72 |
| 3,976,429 | 8/1976 | Ginsbert | 23/259 |
| 3,990,853 | 11/1976 | Godin | 73/864.84 |
| 3,991,055 | 11/1976 | Godin et al. | 436/180 |
| 4,030,888 | 6/1977 | Yamamoto et al. | 23/253 R |
| 4,152,391 | 5/1979 | Cabrera | 73/864.83 |
| 4,445,391 | 5/1984 | Cabrera | 73/864.12 |

FOREIGN PATENT DOCUMENTS 683694 12/1952 United Kingdom .
855482 11/1960 United Kingdom .
907226 10/1962 United Kingdom .

OTHER PUBLICATIONS

Feichtmeir et al., "A Device To Pipet & Dilute Fluid Semi-Automatically," *Am. J. Chemical Pathology*, vol. 35 (4), 378-382, (1961).
Graven et al., "All Teflon Sampling Valve Made for Gas Chromatography," Analytical Chemistry, 1626, (1965).

Primary Examiner—Stewart J. Levy
Assistant Examiner—Robert R. Raevis
Attorney, Agent, or Firm—Limbach, Limbach & Sutton

[57] ABSTRACT

A transfer valve system, method and apparatus are disclosed having a three element valve with a central element sandwiched between front and rear outer elements. Between an aspiration and a discharge position the front and rear outer elements are moved in opposite directions of unequal distances in the same direction with respect to the central member or one outer member and the central member are moved in the same or opposite direction with respect to the other outer member so long as the outer members end up shifted with respect to each other. In the aspiration position, two sample segments are contained in series within the valve. In one embodiment of the invention, one segment is contained within a conduit in the central member and the other segment is contained within a passageway in the rear member. In another embodiment of the invention, the two segments are contained within different conduits of the central member.

25 Claims, 26 Drawing Figures

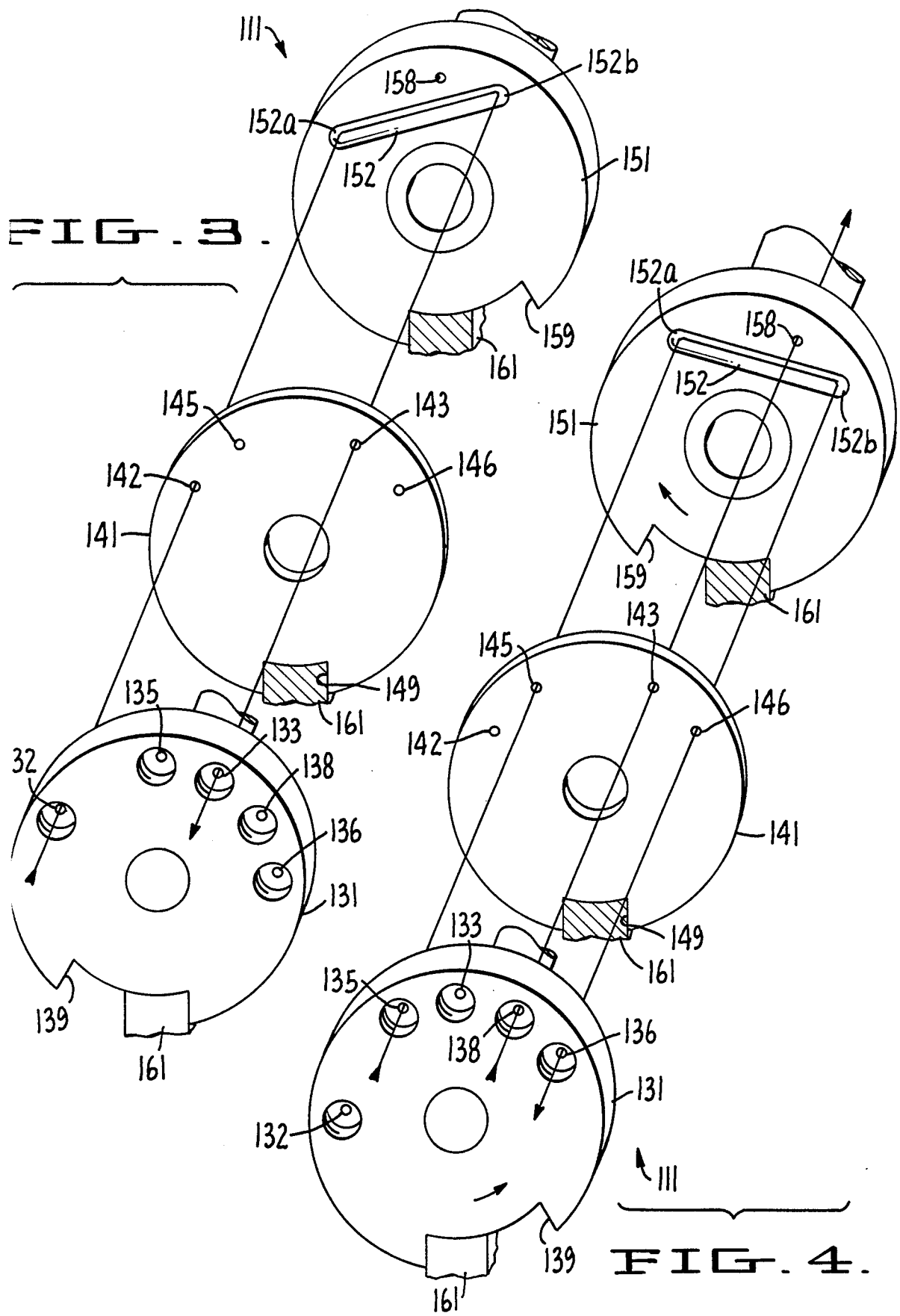

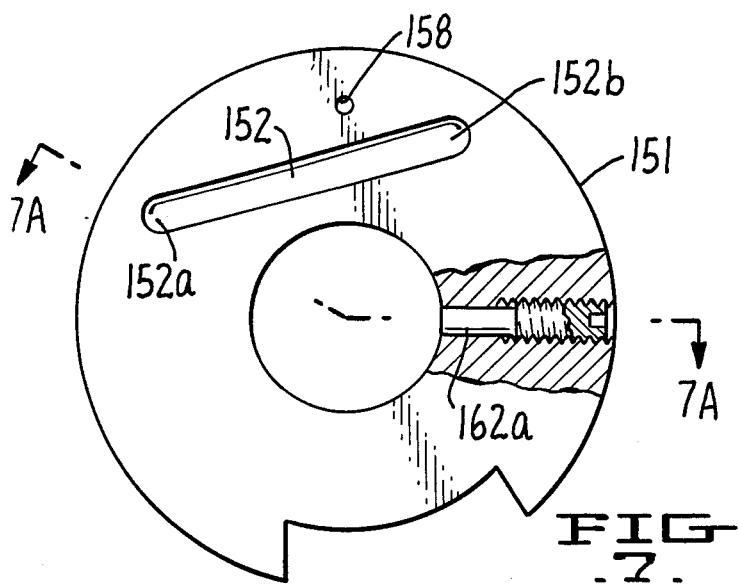
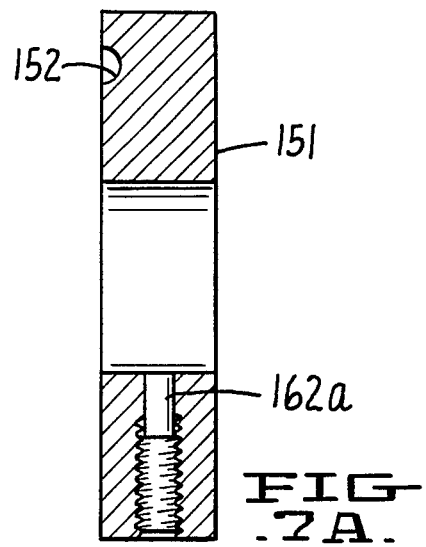
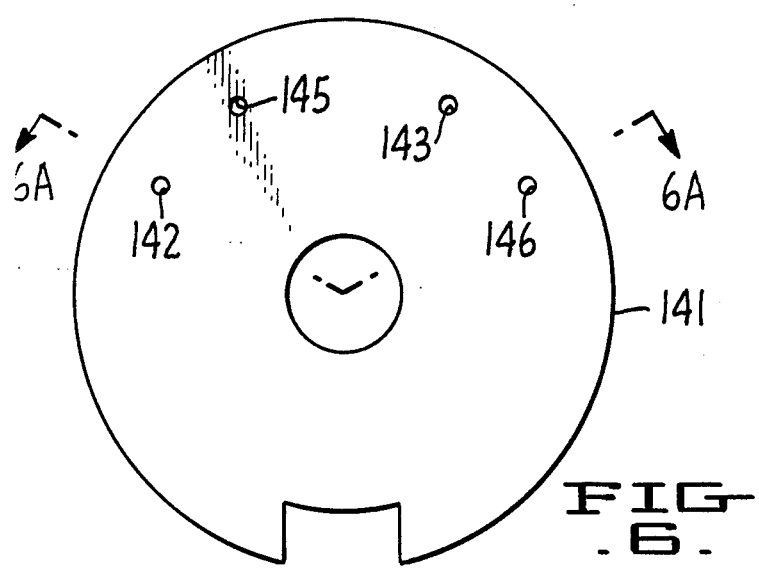
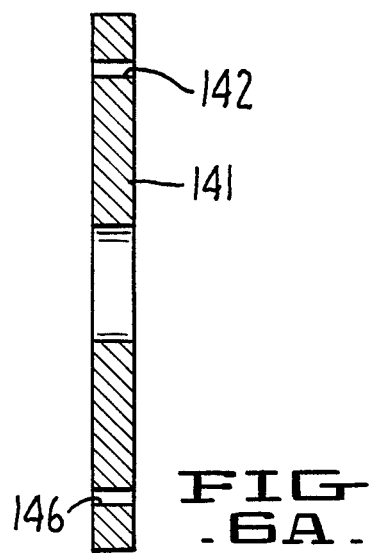
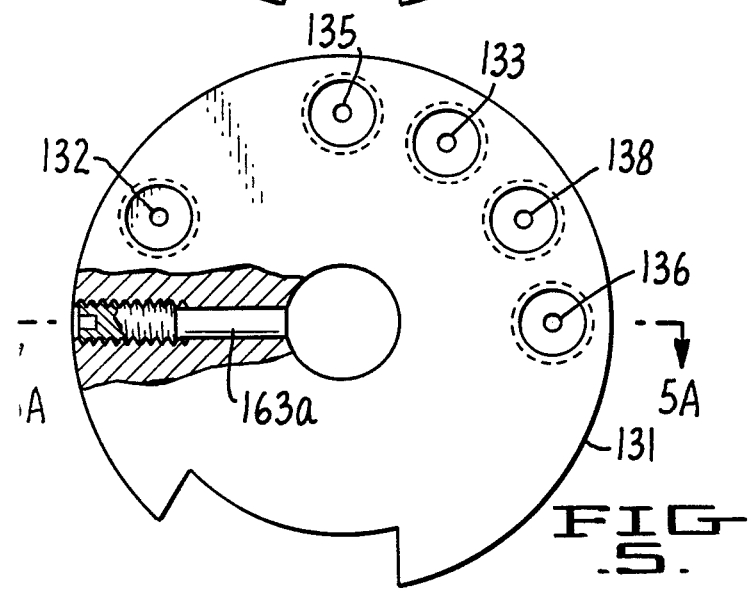
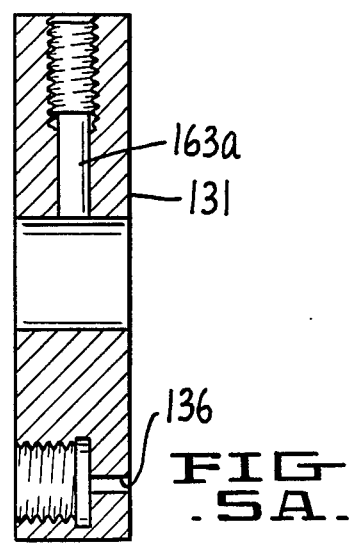

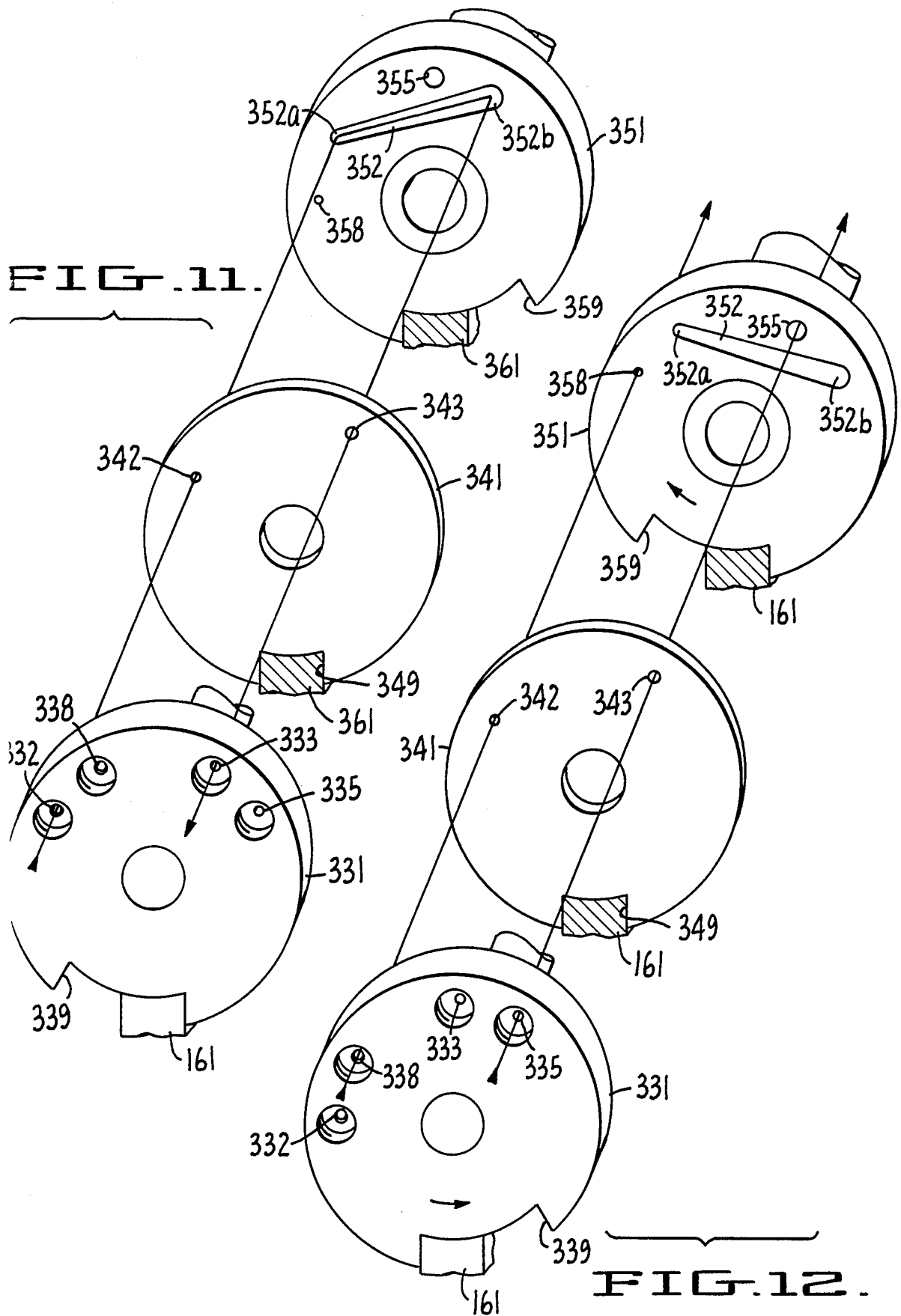

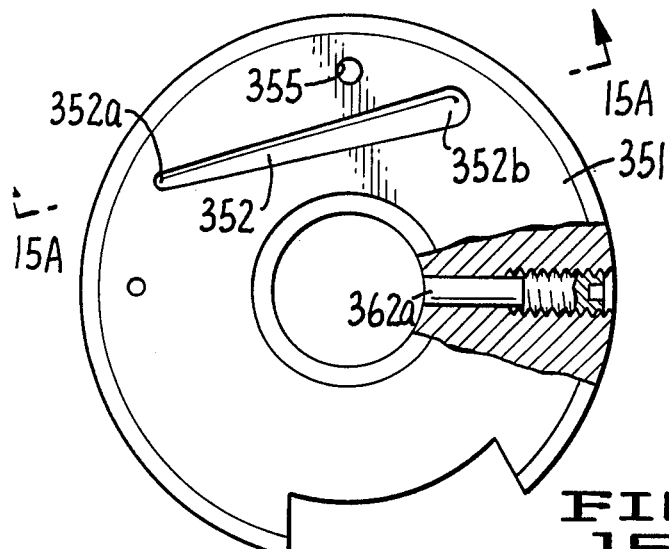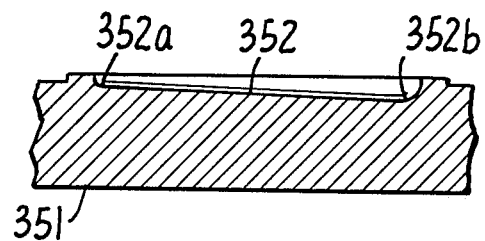
FIG. 15.  FIG. 15A.
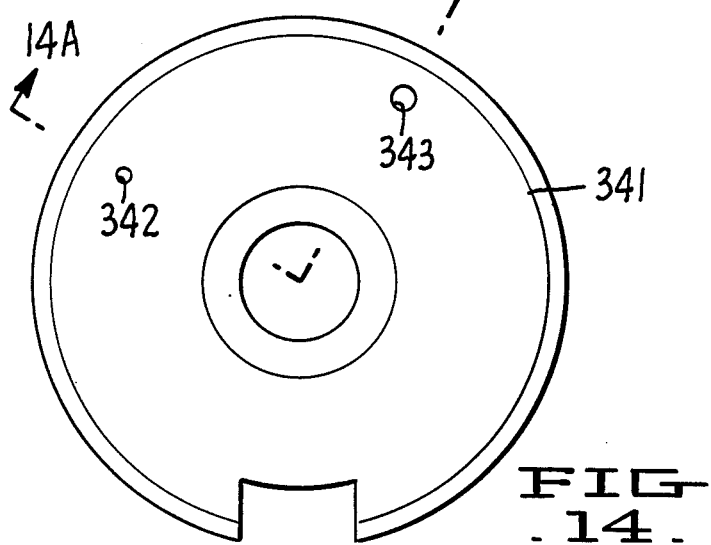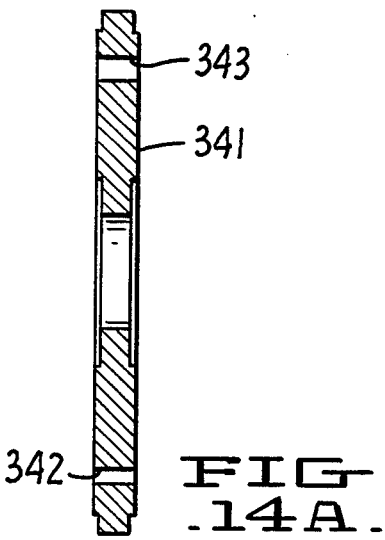
FIG. 14.  FIG. 14A.
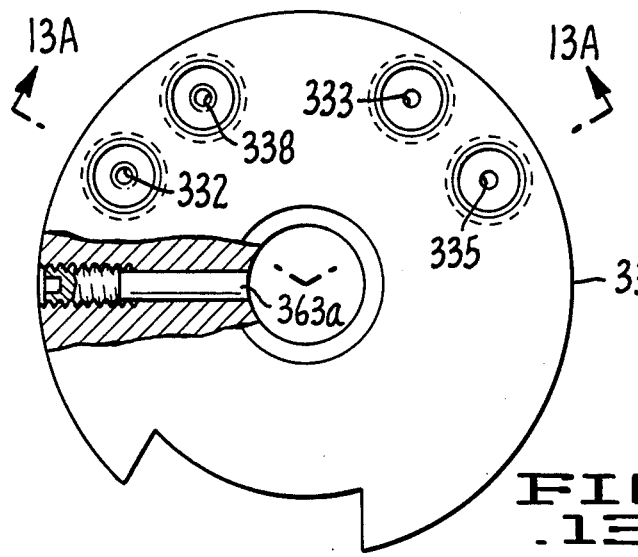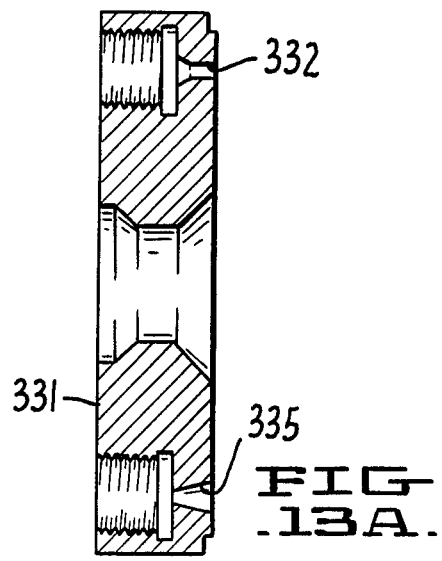
FIG. 13.  FIG. 13A.

FLUID METERING APPARATUS AND METHOD

DESCRIPTION

The present invention relates in general to liquid transfer valves and diluting systems and methods and, more particularly, to methods and apparatus for dilutions of multiple sample segments.

Valves and dilution systems have been used to measure a precise volume of a fluid which is then diluted by adding an externally metered volume of diluent. These valves and systems typically have contained two or three sections which rotate or slide with respect to one another with provision for capturing a precise segment of the sample in a portion of the valve which then moves this segment to a different fluid path. Valves generally disclosing this feature are described and illustrated in U.S. Pat. Nos. 3,652,228, 3,222,135, 3,100,984, 3,131,706, 3,160,015 and 2,846,121.

A particular application for the aforementioned general type of valve is for use in analysis of blood samples and particularly for achieving two blood sample dilutions having different dilution ratios. Some of these valves and systems have required external loops to set the volume. Some have required a thick central section because a line must be connected to this section to allow proper clean out, thereby setting a lower limit on the volume which can be metered by this section. Most of the prior art valves have required multiple passes through them to accomplish a high dilution ratio, and some valves have had to be set in three different positions thereby causing difficult alignment problems. Valves and systems of the aforementioned types are described and illustrated in U.S. Pat. Nos. 3,549,994; 3,567,389; 3,567,390; 3,652,228; 3,976,429, 3,990,853; 3,991,055; 4,030,888; 4,152,391; and 4,445,391.

SUMMARY OF THE INVENTION

The object of the present invention is to provide an improved liquid transfer valve system method and apparatus that easily and simply produces accurate dilutions.

Broadly stated, the present invention, to be described in greater detail below, is directed to a method and apparatus employing at least a three element valve with two elements movable with respect to the third and wherein a sample fluid is directed along a first path through a valve, at least two sample segments along the path are separated and then each of the sample segments is separately diluted thereby providing accurate dilutions from the same sample.

A feature and advantage of this aspect of the present invention is that a maximum number of samples may be taken with a minimum number of valve positions in a valve that is highly accurate and relatively inexpensive to manufacture.

In accordance with this aspect of the present invention, the serially arranged samples along the fluid path provide precise sample segments taken from the same sample fluid.

In accordance with another aspect of the present invention, the sample segments taken along the path may contain different volumes whereby a high dilution ratio can easily be provided with at least one of the sample segments.

In accordance with still another aspect of the present invention, a liquid transfer valve and system are provided utilizing a central member having at least a pair of conduits and a pair of outer members engaged against opposite faces of the central member and movable relative thereto between at least a first and a second position. At least one outer member is provided with at least one passageway (which passageway may be internal or external), connecting between the pair of conduits in the central member in the first position of the valve, and the other outer member having at least a pair of passages each connecting with a different one of the conduits in the first position of the valve. With this construction, separate sample segments can be segregated along the path passing through the valve, first through one passage in the second outer member, then through one conduit of the central member, then through the passageway of the first outer member then through the other conduit of the central member, and finally through the other passage in the second outer member.

In accordance with another aspect of the present invention, the outer members are moved in opposite directions relative to the central member in shifting the valve between different operative positions. This may be accomplished by holding the central member fixed while rotating or translating the outer members in opposite directions equal or unequal distances or in the same direction unequal distances.

Alternatively, one outer member can be held fixed while moving the central member and other outer member in the same direction, one more than the other with respect to the fixed outer member or in opposite directions so long as the outer members end up shifted with respect to each other.

In accordance with one embodiment of the present invention, as aforementioned, one sample segment is captured in one of the conduits of the central member and an other sample segment is captured in the passageway of the outer member. A third sample segment may be captured in another conduit of the central member.

In accordance with one embodiment of the present invention, the central member has a second pair of conduits communicating with the passageway of the first outer member in the second position and the second outer member has a second pair of passages communicating with the second pair of conduits in the second position for producing a first dilution. Also, the first and second outer members have an additional passage communicating with one of the first pairs of conduits in the second position for producing a second dilution.

In accordance with this embodiment of the present invention, a liquid transfer valve and system method and apparatus are provided which can be easily manufactured and precisely produced to provide precise sample segments by one alteration in the position of the valve, with the sample segments being of different volumes as normally required.

In accordance with still another embodiment of the present invention, a pair of sample segments are produced in the two conduits of the central member of the aforementioned valve method and apparatus. In accordance with this embodiment of the present invention, the first outer member has a pair of passages communicating with the central member conduits in the second position of the valve, and the first outer member has a second pair of passages also connecting with the central member conduits in the second position of the valve.

This embodiment of the present invention also provides an accurate, easy to manufacture transfer valve method and apparatus wherein the central member conduits contain different sample volumes for producing different dilutions.

These features and advantages of the present invention will become more apparent upon a perusal of the following specification taken in conjunction with the accompanying drawings wherein similar characters of reference refer to similar structures in each of the separate views.

BRIEF DESCRIPTION OF THE DRAWINGS

FIG. 3 is an isometric exploded view of the aspirator position of a rotary valve incorporating features of the valve of FIG. 1.

FIG. 4 is a view similar to FIG. 3 with the valve in delivery position.

FIGS. 5 and 5A are a front plan view, partially broken away, of the front member of the valve in FIGS. 3 and 4.

FIGS. 6 and 6A are a front plan view of the central member of the valve shown in FIGS. 3 and 4.

FIGS. 7 and 7A are a front plan view, partially broken away, of the rear member of a valve shown in FIGS. 3 and 4.

FIG. 11 is an isometric exploded view of a rotary valve incorporating the features of the valve in FIGS. 9 and 10 and positioned in the aspirator position.

FIG. 12 is a view similar to FIG. 11 with the valve in delivery position.

FIG. 13 is a front plan view of the front member of the valve shown in FIGS. 11 and 12.

FIG. 13A is a cross-sectional view of a portion of the structure shown in FIG. 13, taken along the line 13A—13A in the direction of the arrows.

FIG. 14 is a front plan view of a central member of the valve shown in FIGS. 11 and 12.

FIG. 14A is a cross-sectional view of a portion of the structure shown in FIG. 14 taken along the line 14A—14A in the direction of the arrows.

FIG. 15. is a front plan view of the rear member of the valve shown in FIGS. 11 and 12.

FIG. 15A is a cross-sectional view of the a portion of the structure shown in FIG. 15 taken along the line 15A—15A in the direction of the arrows.

DESCRIPTION OF THE PREFERRED EMBODIMENT

While the present invention is directed to a transfer valve and system method and apparatus having many applications, its principle application is for providing blood sample dilutions for red blood cell and platelet counts and white blood cell counts which are treated in one or more of the methods referred to in the prior art referenced above. Accordingly, the present invention will be described with respect to an embodiment illustrating a manner of producing white blood cell and red blood cell and/or platelet dilutions of different concentration of sample fluid.

Figure 1:
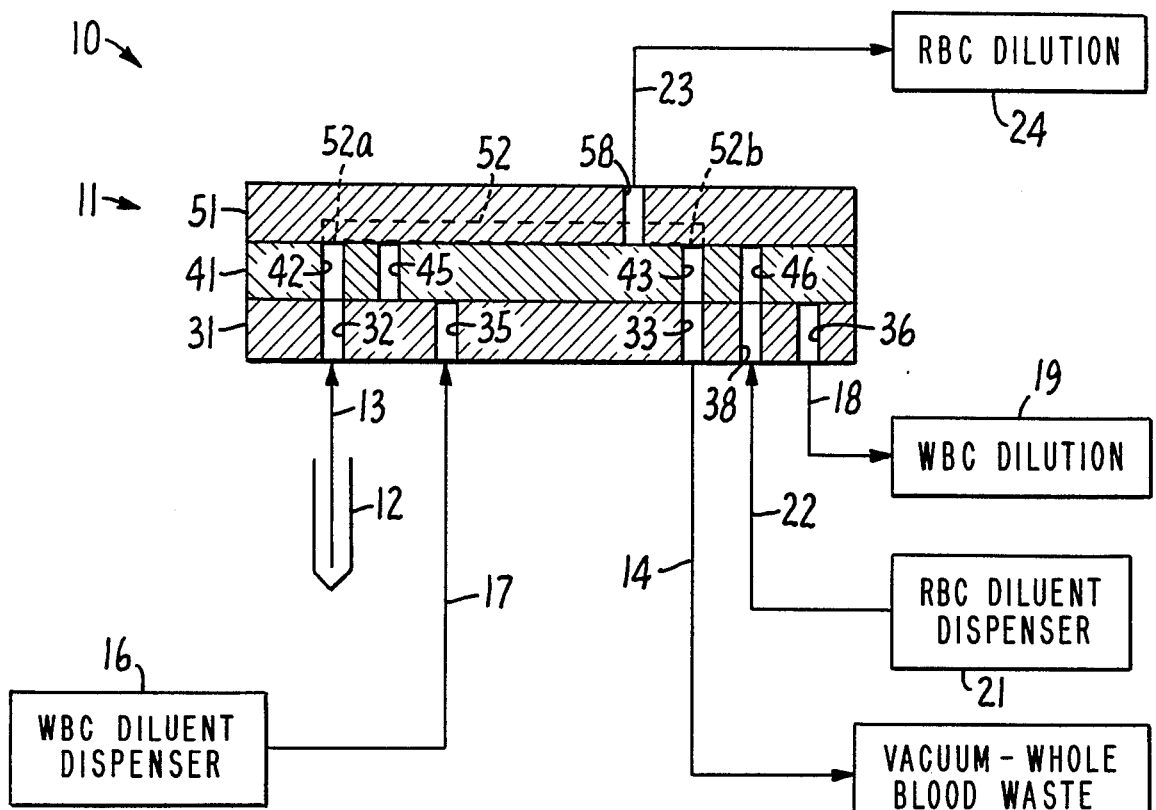
FIG. 1 is a side elevational schematic view of one valve embodiment of the present invention in the aspirator position.
Figure 2:
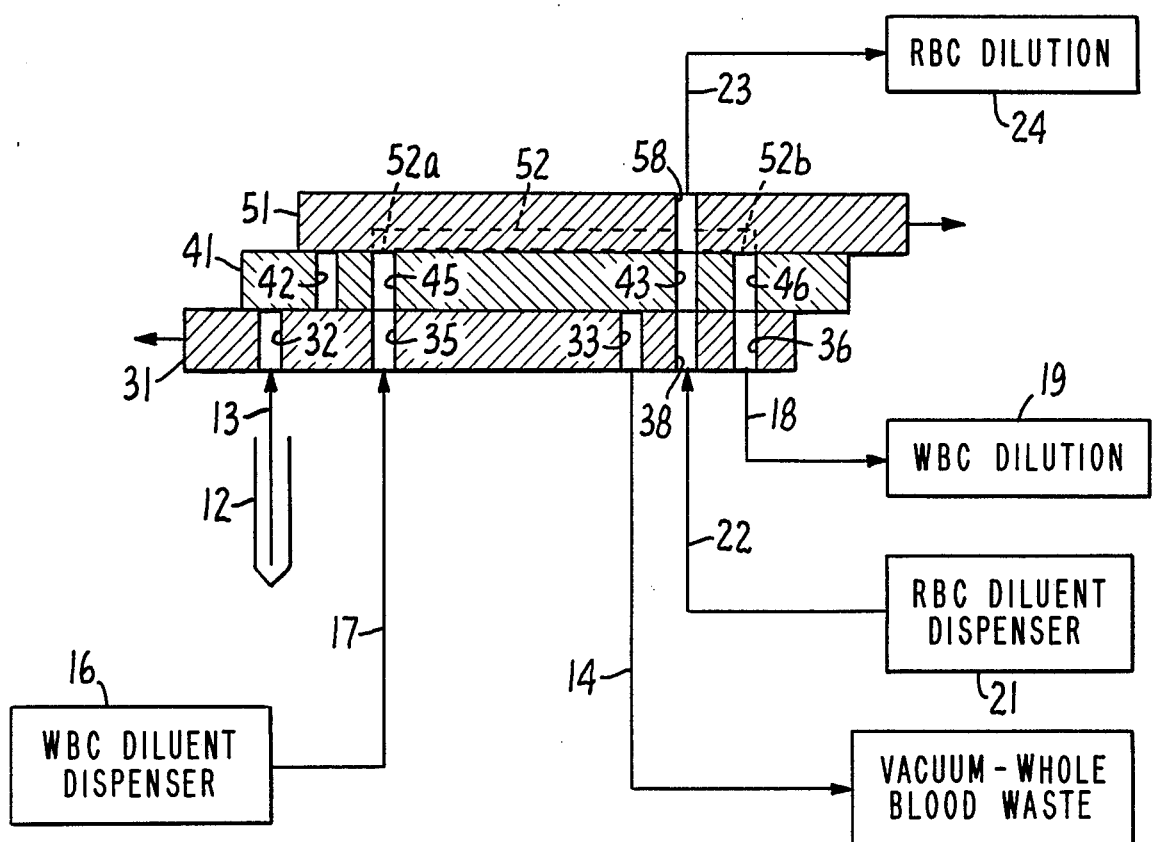
FIG. 2 is a view similar to FIG. 1 with the valve in delivery position.

Referring now to FIGS. 1 and 2, there is schematically illustrated a slide valve version of a first embodiment of the present invention wherein a dilution system 10 is provided for an automatic blood analyzing system wherein sample blood dilutions are made for white blood cell count and red blood cell/platelet count determinations having different dilution ratios and which are then operated on fully automatic by other apparatus.

The system 10 includes a transfer valve 11 for receiving a sample fluid such as whole blood from an aspirator tube 12 via line 13 and drawn into the valve by means of a vacuum at a whole blood waste station 15 connected to the valve via line 14.

A white blood cell diluent dispenser 16 is connected via line 17 to the valve and a line 18 leads the white blood cell dilution 19 from the valve for analysis.

Similarly, a red blood cell/platelet diluent dispenser 21 is connected to the valve 11 via line 22, and line 23 leads the red blood cell dilution 24 from the valve for analysis.

The transfer valve 11 itself comprises a central member 41 sandwiched between a front outer member 31 and a rear outer member 51 in close sliding relationship so that certain communication paths in the several members can be provided in a particular communication arrangement in a first position of the valve shown in FIG. 1 and in a second position of the valve shown in FIG. 2. As shown, the valve is designed such that the front and rear outer members 31 and 51, respectively, move in opposite directions relative to the central member in moving from the first, aspirator position to the second delivery position. It will, of course, be appreciated by those skilled in the art that, under certain conditions, it might be desirable and is possible for the central member to move as the valve is shifted from the aspiration to the delivery position. For example, one of the outer members could be held fixed while the other outer member and the center section are moved in the same direction or in opposite directions so long as the outer members end up shifted with respect to one another.

The central member 41 has a first pair of spaced apart conduits 42 and 43 to aid in establishing a path for the fluid sample through the valve in the aspirator position. Central member 41 also has a second pair of spaced apart conduits 45 and 46 for aid in the delivery of the segregated samples in the manner set forth below.

The front outer member 31 has a pair of spaced apart passages 32 and 33 which can be described as a blood aspirator inlet passage 32 and blood aspirator outlet passage 33 which respectively are aligned with and communicate with central member conduits 42 and 43 in the first position of the valve shown in FIG. 1. Line 13 is provided in fluid communication with passage 32 and line 14 is provided in fluid communication with passage 33.

The front outer member 31 also has a second pair of spaced apart passages 35 and 36 which are provided in fluid communication with the white blood count diluent dispenser line 17 and the white blood count dilution line 18, respectively. In the aspirator position of the valve, shown in FIG. 1, passages 35 and 36 do not communicate with any of the central member conduits 42, 43, 45, and 46, in the first position, but in the delivery position of the valve shown in FIG. 2 passages 35 and 36 communicate with conduits 45 and 46, respectively.

The front outer member 31 also includes a red blood cell/platelet diluent inlet passage 38 which in the delivery position valve communicates with central member conduit 43.

Rear outer member 51 is provided with a laterally extending passageway 52 extending between openings 52a and 52b in the face adjacent the central member 41 and communicating with both central member conduits 42 and 43 in the aspirator position of the valve. The rear outer member 51 also includes a through passage 58 serving as the red blood cell dilution discharge in communication with central member conduit 43 in the discharge position of the valve.

In operation of the valve, first in the aspirator position, shown in FIG. 1, whole blood is drawn from tube 12 via line 13 through and to fill passage 32, conduit 42, passageway 52, conduit 43, and passage 33 while being drawing via vacuum line 14 to be disposed of as whole blood waste 15. In this embodiment of the invention, sample segments of the blood are trapped in passage 52 for the white blood cell dilution and in conduit 43 for the red blood cell/platelet dilution.

The outer members 31 and 51 of valve 11 are then shifted, relative to the central member 41, to the delivery position shown in FIG. 2. A precise amount of white blood cell diluent is forced from dispenser 16 through line 17, passage 35, conduit 45, passageway 52, conduit 46, passage 36, and via line 18 as the white blood cell dilution. As this diluent passes through the valve, it forces ahead of it into the white blood cell dilution the blood sample segment that had been contained in the passage 52.

Similarly, in a discharge position shown in FIG. 2, a precise volume of red blood cell/platelet diluent is passed from dispenser 21 via line 22 through passage 38, conduit 43, and passage 58 to emerge via line 23 as the red blood cell dilution 24. In passing through the valve, this diluent moves the previously trapped blood sample segment from the central element conduit 43 for the precise red blood cell dilution. The sample segments are taken in series from the fluid sample which is drawn in and through the valve 11.

It will be appreciated that the volume contained by passageway 52 is much greater than the volume contained by conduit 43 so that different desired dilutions are easily obtained simultaneously with this valve and system.

It will be appreciated by those skilled in the art that passages 38 and 58 could have been arranged for alignment and communication with central member conduit 42 instead of central member conduit 43 for producing the red blood cell/platelet dilution. Also, the blood sample segment contained in central member conduit 42 could be used with a different pair of passages in the two outer members for producing a third dilution, and the volumes contained by conduits 42 and 43 could be made to be different so that a third dilution with a substantially different dilution ratio could be easily obtained.

Referring now to FIGS. 3-8, there is shown a cylindrical rotational version 111 of the sliding valve embodiment 11 schematically illustrated in FIGS. 1-2. As shown in FIGS. 3-8, the same reference numbers are used to refer to the same valve elements, passages and conduits as shown in FIGS. 1 or 2, but with an additional one hundred digit added.

As illustrated, the central valve member 141 and the front and rear outer valve members 131 and 151 are annular discs with the respective passages, conduits and passageway ends, described with respect to the linear embodiment of FIGS. 1 and 2, located at the same radial distance from the centers of the discs. In the aspirator position of the valve 111 shown in FIG. 3, front disc passage 132 and rear disc opening 152a to passageway 152 communicate with the central disc conduit 142 while front disc passage 133 and rear disc opening 152b communicate with the central disc conduit 143. In the delivery position shown in FIG. 4 front disc passage 135 and rear disc opening 152a communicate with central disc conduit 145, and front disc passage 136 and rear disc opening 152b communicate with central disc conduit 146. Additionally, front disc passage 138 and rear disc passage 158 communicate with central disc conduit 143.

The passageway 152 is shown in FIGS. 3-7 as a groove formed in rear member 151 with the length of the groove 152 being closed by the abutting surface of the central member 141.

The disc elements 131, 141 and 151 are supported in a drive assembly which includes a rigid stop member 161 aligned with the rotational axis of the valve members 131, 141, and 151 but spaced radially outward therefrom for engaging the edges of circumferential notches 139, 149, and 159 in the members 131, 141, and 151, respectively. The circumferential notch 149 of the central member is the same size as the stop member thereby preventing any rotation of the central member whereas the circumferential notches 139 and 159 of the outer members 131 and 151 permit rotation, such as, for example, 30°, rotation of those members with respect to the central member.

Figure 8:
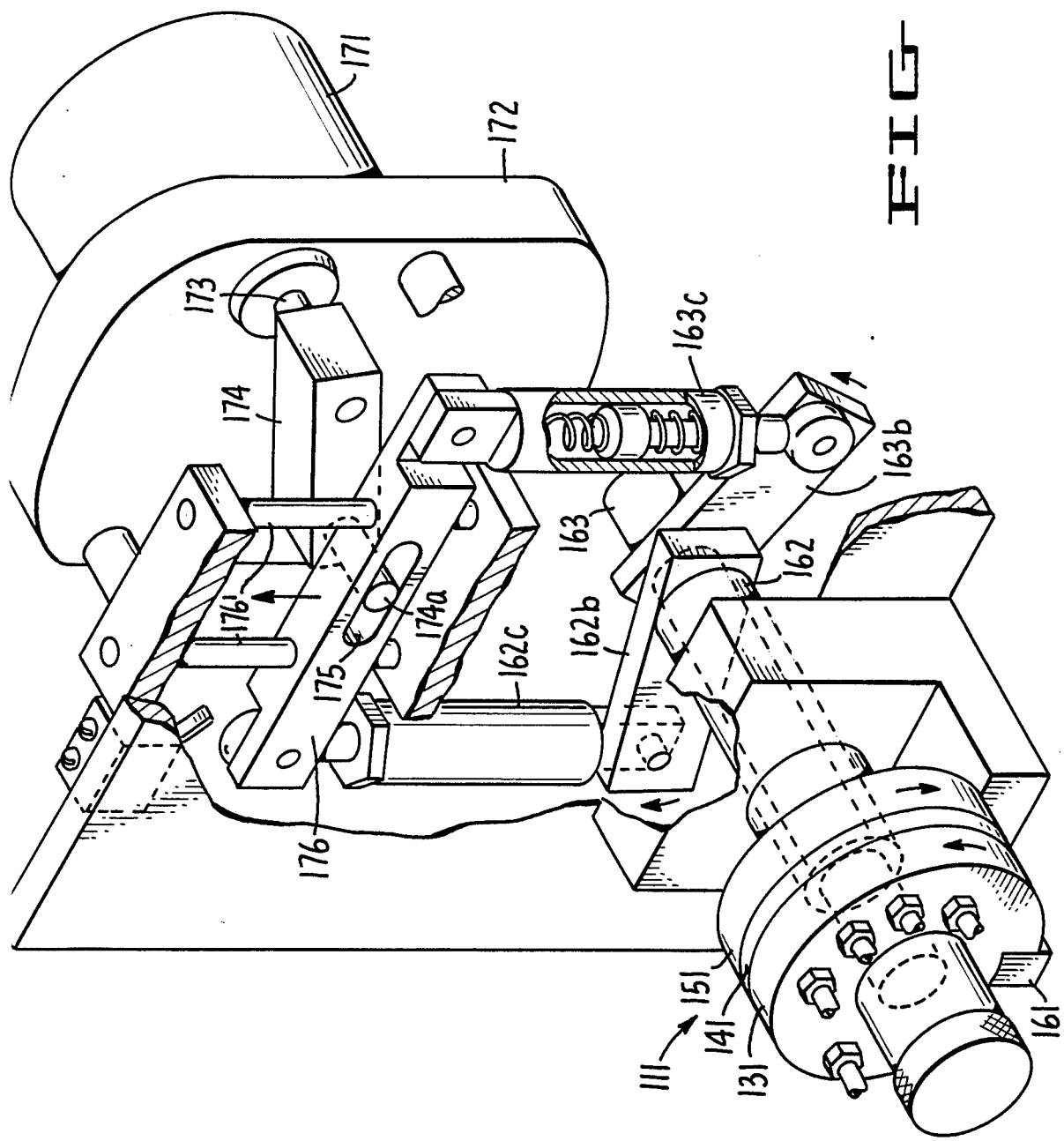
FIG. 8 is an isometric exploded view of a drive mechanism for rotating the outer members of the valve shown in FIGS. 3 and 4.

The drive assembly shown in FIG. 8 for producing the opposite rotation of the outer members with respect to the central member includes a pair of concentric outer and inner drive shafts 162 and 163, respectively, which pass through apertures in the respective rear and front valve members 151 and 131, respectively, for engagement by set screws 162a and 163a radially through these respective valve members to fix the valve members to the respective drive shafts. Levers 162b and 163b are clamped to the drive shafts 162 and 163, respectively, for causing rotation thereof in accordance with the action of a drive assembly described below. The levers 162b and 163b project away from the shafts 162 and 163 in opposite directions.

The driving mechanism includes a drive motor 171 mounted on a gear box 172 having an output drive shaft 173 having a crank 174 connected thereto. The crank 174 has a pin 174a positioned in a slot opening 175 in a bar 176 which is vertically, slidably supported on a pair of rods 176' and which has its opposite ends pinned to the free ends of the drive levers 162b and 163b by pins 162c and 163c respectively.

The valve is operated automatically by the motor 171. The motor 171 causes the drive shaft 173 to rotate the crank 174. The crank 174, via the pin 174a moves the bar 176 vertically causing levers 162b and 163b to pivot in opposite directions, thereby causing the valve member drive shafts 162 and 163 to rotate the valve outer members 131 and 151 in opposite directions between the aspirator and discharge portions shown in FIGS. 3 and 4.

Figure 9:
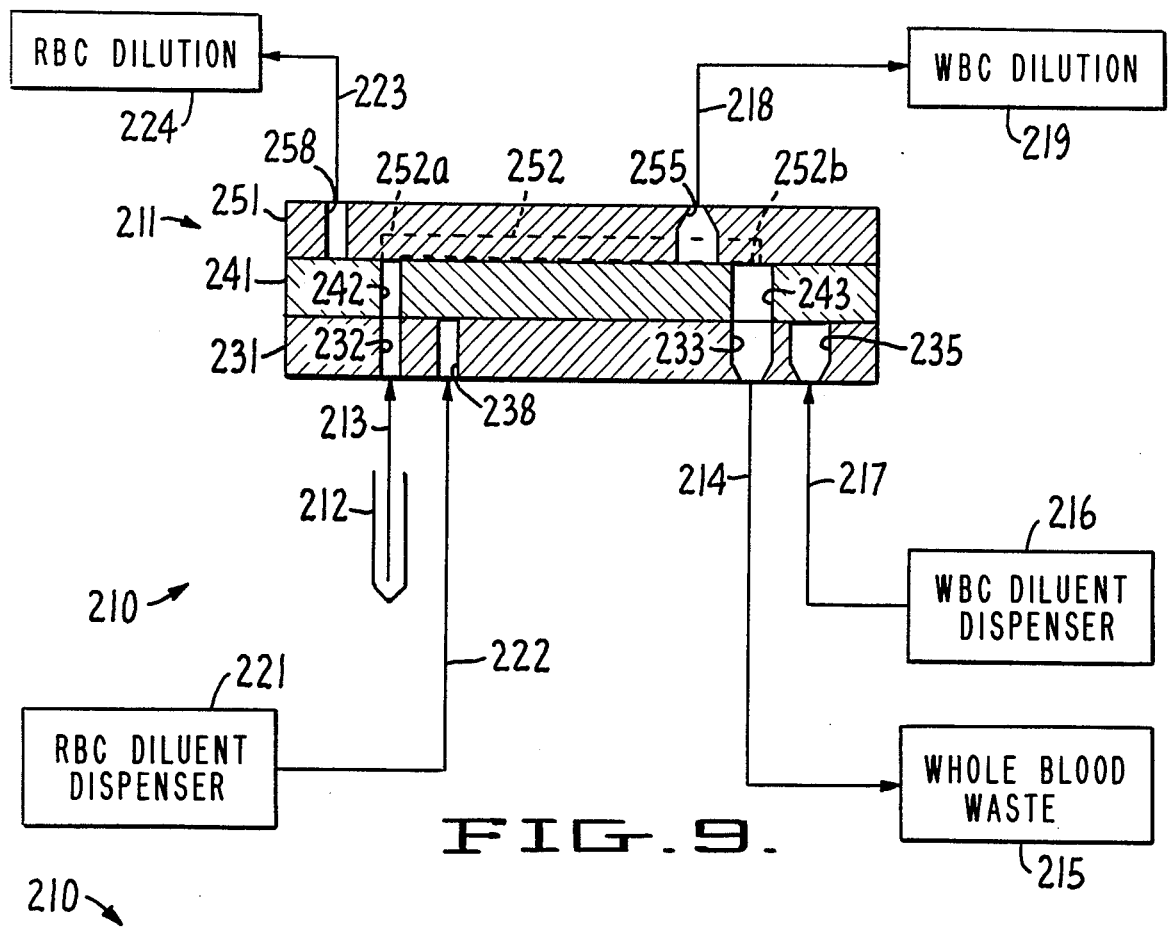
FIG. 9 is a schematic elevational sectional view of a valve in accordance with another embodiment of the present invention and with the valve positioned in the aspirator position.
Figure 10:
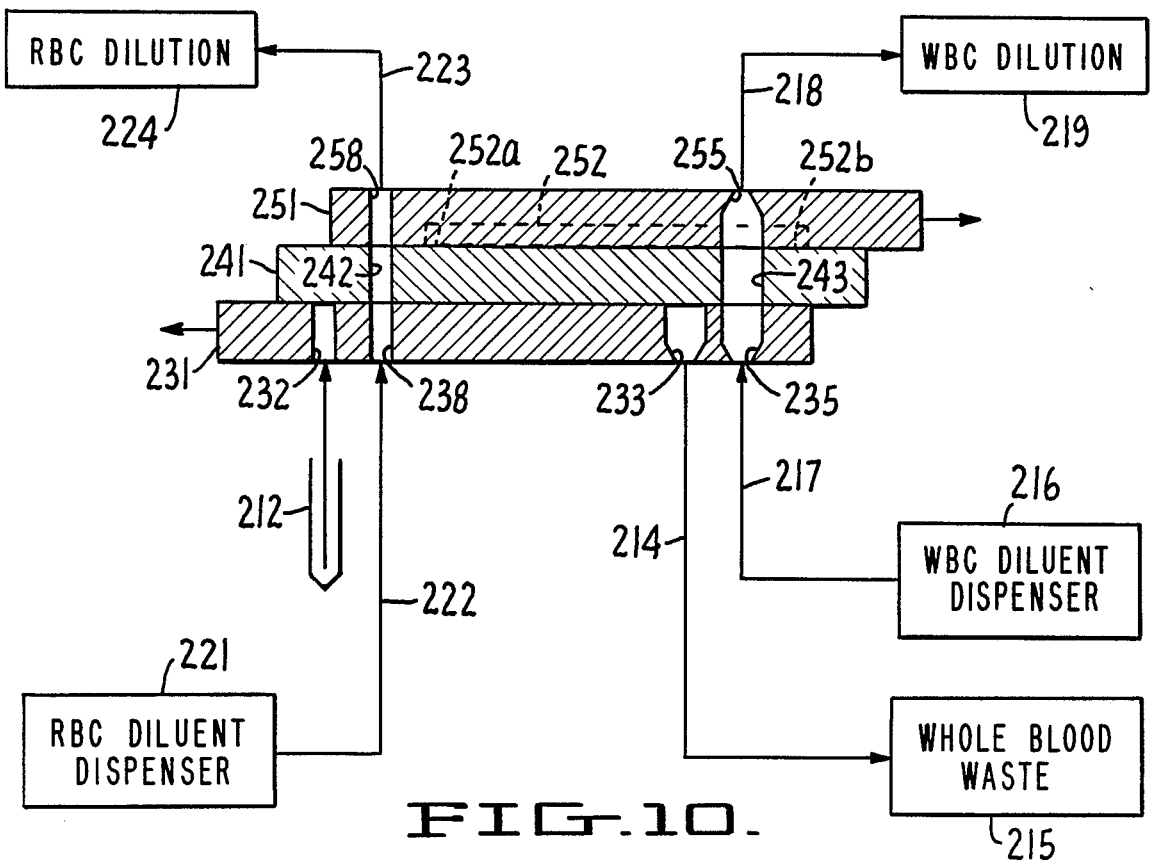
FIG. 10 is a view similar to FIG. 9 with the valve in the delivery position.

Referring now to FIGS. 9 and 10, there is shown the sliding version of an alternative embodiment of the present invention wherein the sample segments are separated in two conduits of the central member of a three member sandwiched valve. This valve and its associated system are illustrated with reference numbers similar to the numbers of FIGS. 1 and 2 but with an additional two hundred digit number added. The dilution system 210 shown in FIGS. 9 and 10 includes a valve 211 connected via line 213 to a whole blood aspirator 212, via line 214 to the whole blood waste 215, via a line 217 to a white blood count diluent dispenser 216, via line 218 to a white blood count dilution path 219, via line 222 to a red blood count diluent dispenser 221 and via line 223 to a red blood count dilution path 224. Although valve 211 is constructed differently from the previously described embodiments, it also operates on the principle of movement of the front and rear members 231 and 251 in opposite directions relative to the central member 241.

The front outer member 231 includes a pair of passages 232 and 233 which are connected to the whole blood aspirator tube 212 and whole blood waste 215 via lines 213 and 214, respectively. In the aspirator position (shown in FIG. 9), these passages 232 and 233 communicate with conduits 242 and 243 through the central valve member 241. The front valve member has an additional pair of passages 235 and 238 which are connected respectively to the white blood cell diluent dispenser 216 via line 217 and the red blood cell/platelet diluent dispenser 221 via line 222. In the discharge position of the valve 211 (shown in FIG. 10), passages 235 and 238 communicate with central member conduits 243 and 242, respectively.

The rear outer member 251 has a laterally extending passageway 252 connecting at its ends 252a and 252b with central member conduits 242 and 243, respectively, in the aspirator position. The rear outer member 251 also has two other through passages 255 and 258. Passage 258 communicates via line 223 for discharge of the red blood cell dilution 224. Passage 255 discharges the white blood cell dilution 219 via line 218. Passage 258 communicates with conduit 242 only in the discharge position of the valve, and passage 255 communicates with conduit 243 only in the discharge position of the valve. In the valve of this embodiment, the two different sample segments are separated in the conduits 242 and 243, and accordingly for different dilution ratios, these conduits are of different size.

In the aspirator position of the valve, shown in FIG. 9, whole blood is drawn along a path in from the tube 212 via line 213 to fill first passage 232, then conduit 242, then passageway 252, then conduit 243, and then passage 233 as the whole blood is drawn via line 214 to waste 215. When the outer members 231 and 251 of valve 211 are shifted in opposite directions with respect to the central member 241 to the discharge position, sample segments captured in conduits 242 and 243 are placed in different paths for the desired dilutions.

In the discharge position shown in FIG. 10, front outer member passage 238 and rear outer member passage 258 are placed in communication with conduit 242, and front outer member passage 235 and rear outer member passage 255 are placed in communication with conduit 243. The white blood cell diluent from dispenser 216 is pushed through line 217 and passage 235, then conduit 243, and then passage 255 pushing the sample segment previously trapped in conduit 243 into the white blood cell dilution 219.

Similarly, red blood cell/platlet diluent is passed from dispenser 221 via line 222 first through passage 238, then conduit 242, and then passage 258, pushing the sample segment formerly in conduit 242 to the red blood cell/platelet count dilution 224.

The cylindrical version of the embodiment of FIGS. 9 and 10 is illustrated in FIGS. 11–15 with the corresponding parts preceded by a three hundred digit number instead of a two hundred digit. Similar to the cylindrical version in FIGS. 3–7 of the embodiment shown in FIGS. 1 and 2, the passages, conduits and ends of passageway in the central valve member 341 and the front and rear outer valve members 331 and 351 are located centered on a common radius of curvature about the axes of their respective members. FIGS. 11–15 show typically respective sizes for the passages, conduits and passageways to produce appropriate dilutions with different dilution ratios. By way of example a valve producing in accordance with this aspect of the present invention has produced dilutions as high as 1:12,500 and as low as 1:250 simultaneously. Dilution precision (measured with multiple blood samples on a laboratory cell-counting system) has been determined to be better than 1% coefficient of variation (CV) for both dilutions. Furthermore, carry-over of one sample into the next has also been measured to be less than 1%. An operative embodiment of this invention can be made of appropriate materials such as, for example, alumina ceramic valve members which slide with respect to one another and produce appropriate seals therebetween for making the desired connection between conduits, passages and passageway.

In the embodiments of the invention illustrated in FIGS. 1–15 the two outer members are moved the same amount in opposite directions relative to the central member in moving the valve from the first to the second position. The present invention contemplates other possible movements of the outer members with respect to the central member, or one outer member and the central member with respect to the other outer member for operating the valve to produce a maximum number of samples with a minimum number of valve positions.

Figure 16:
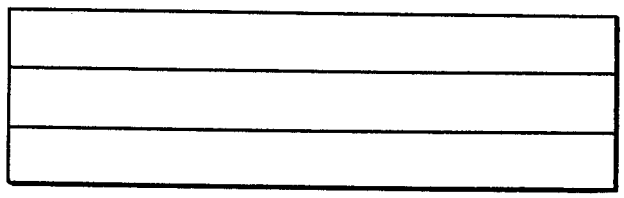
FIGS. 16-16D are side elevational schematic views illustrating different valve movements incorporating features of the present invention.
Figure 16A:
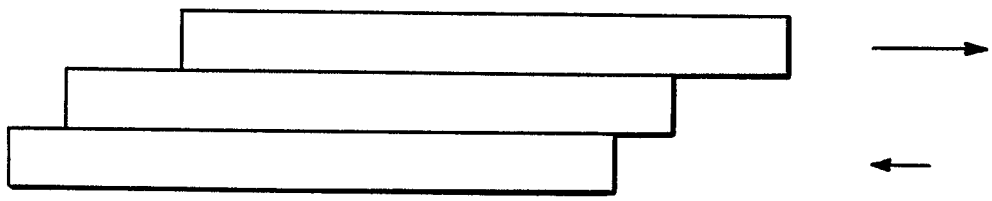
Figure 16B:
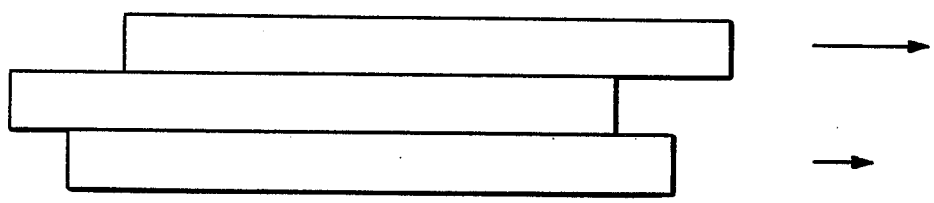
Figure 16C:
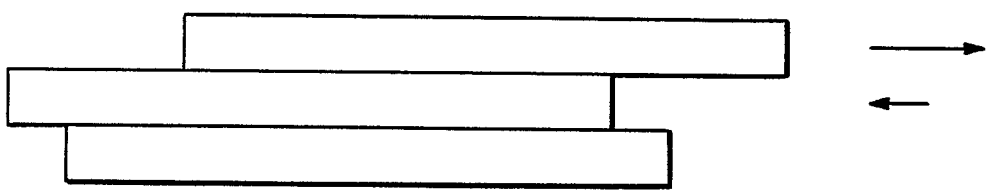
Figure 16D:
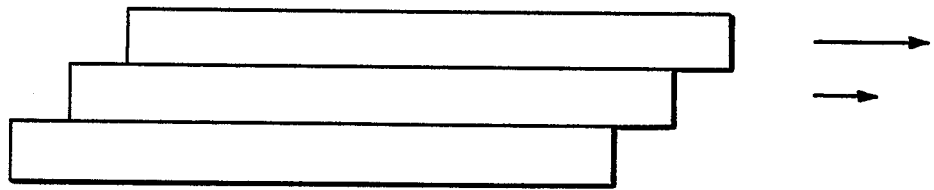

Referring now to FIGS. 16–16D there are shown other embodiments of the present invention. In 16 the valve elements are shown in a first position similar to that shown in FIGS. 1 and 9. FIGS. 16A–16D illustrate various movements of the valve elements to the second position. While these movements are illustrated as translational, the movements could also be rotational. Therefore, the term "move" will be used to mean either translational or rotational action.

FIG. 16A illustrates movement of the outer members one more than the other in opposite directions relative to the central member and FIG. 16B illustrates movement of the outer members one more than the other in the same direction relative to the central member.

FIG. 16C illustrates movement of one outer member and the central member one more than the adjacent other in opposite directions. FIG. 16D illustrates movement of one outer member and the central member in the same direction with respect to the other outer member.

It will be appreciated by a person skilled in the art that the present invention encompasses movement of at least two of the three members and that the third member can also be moved so long as the same relative movement of the first two members with respect to the third member is still accomplished.

The terms and expressions which have been employed here are used as terms of description and not of limitations, and there is no intention, in the use of such terms and expressions, of excluding equivalents of the features shown and described, or portions thereof, it being recognized that various modifications are possible within the scope of the invention claimed.

I claim:

1. A transfer valve for use in an automatic diluting system for a sample fluid comprising, in combination:
   a central member having at least a pair of conduits,
   a pair of outer members engaged against oposite faces of such central member and movable in opposite directions with respect thereto between at least a first and a second position,
   means for moving said outer members in opposite directions relative to said central member in moving between said first and said second positions,
   at least one of said outer members having at least one internal or external passageway connecting said pair of conduits in said first position,
   the other of said outer members having at least a pair of passages each connecting with a different one of said conduits in said first position, and
   said passages, passasgeway and conduits forming a path through said valve for capturing separate sample segments along separate parts of said path.

2. The transfer valve of claim 1 wherein said members in said first position define a fluid path beginning and ending at the non-engaging face of said other outer member and passing through one of said pair of passages, then through one of said conduits, then through said passageway, then through the other of said conduits and then through the other of said pair of passages.

3. The transfer valve of claim 1 wherein said members are hollow cylindrical members and including oppositely rotating drive shafts for rotating said outer members in opposite directions.

4. The transfer valve of claim 1 wherein separate segments are captured in each of said conduits.

5. The transfer valve of claim 4 wherein said one outer member has a pair of passages each connecting with a different one of said conduits in said second position and wherein said other outer member has a second pair of passages each connecting with a different one of said conduits in said second position.

6. The transfer valve of claim 4 wherein said other outer member has a second pair of passages each connecting with a different one of said conduits in said second position.

7. The transfer valve of claim 1 wherein said one outer member has a pair of passages each connecting with a different one of said conduits in said second position.

8. The transfer valve of claim 1 wherein said conduits contain different volumes.

9. The transfer valve of claim 1 characterized by said members in said first position defining a fluid path beginning and ending at the non-engaging face of said other outer member and passing through one of said pair of passages, then through one of said conduits, then through said passageway, then through the other of said conduits and then through the other of said pair of passages, said one outer member having a pair of passages each connected to a sample treatment path and each connecting with a different one of said conduits in said second position, one sample segment being captured in each of said conduits.

10. The apparatus of claim 9 wherein said other outer member has a second pair of passages each communicating with a different one of said conduits in said second position.

11. The transfer valve of claim 1 wherein one segment is captured in one of said conduits and another segment is captured in said passageway.

12. The transfer valve of claim 11 wherein said one conduit and said passageway are of different volumes.

13. The transfer valve of claim 11 wherein said central member has a second pair of conduits connecting with said passageway in said second position and wherein said other outer member has a second pair of passages each connecting with a different conduit of said second pair of conduits in said second position.

14. The transfer valve of claim 11 wherein said one conduit and said passageway are of different volumes, said central member has a second pair of conduits connecting with said passageway in said second position, and said other outer member has a second pair of passages each connecting with a different conduit of said second pair of conduits in said second position.

15. A transfer valve for use in an automatic diluting system for a sample fluid comprising, in combination,
    a central member having at least a pair of conduits and
    a pair of outer members engaged against opposite faces of said central member and movable in opposite directions relative to said central member between a first and a second position,
    one of said outer members having two pairs of passages, each pair of passages associated with a different conduit and each pair of passages having one passage connecting with the associated conduit in said first position,
    the other of said outer members having a passageway connecting said conduits in said first position,
    said members in said first position capturing sample segments of fluid in series by defining a fluid path beginning and ending with the passages connecting with the conduits and including between said passages along said path said conduits and said passageway.

16. The valve of claim 15 wherein said other outer member has a pair of passages each for communicating with a separate sample segment processing path, in said second position each of said pair of passages in said other outer member connecting with a different one of said conduits to deliver a sample segment to the processing path.

17. The valve of claim 16 wherein said conduits contain different volumes.

18. The valve of claim 15 wherein said central member has a second pair of conduits and each of said outer members has another passage connecting in said second position with the same conduit of the first pair of conduits whereby one sample segment is delivered from said one conduit by a path through said other passages and another sample segment is delivered from said passageway by a path through the second pair of conduits and passages in said one outer member connecting with said second pair of conduits in said second position.

19. A transfer valve for use in an automatic diluting system for a sample fluid comprising, in combination,
    a central member having a pair conduits, and a pair of outer members engaged against opposite faces of said central member, said outer members movable in opposite directions relative to said central member between a first and a second position, one of said outerr members having two pairs of passages, each pair o passages associated with a different conduit and each pair of passages having one passage connecting with the associated conduit in said first said position and the other passage connecting with the associated conduit in the second position, one passage of said two pairs of passages for receiving the sample fluid, the other of said outer members having a passageway connecting said conduits in said first position and having a pair of passages each connecting with a different one of said conduits in said second position.

20. A transfer valve for use in an automatic diluting system for a sample fluid comprising, in combination, a central member haivng an aspirator pair of conduits and a delivery pair of conduits and a pair of outer members engaged against opposite faces of said central member and movable in opposite directions between an aspirator position and a delivery position, a first of said outer members having an aspirator pair of passages connecting with said aspirator pair of conduits in said aspirator position and a delivery pair of conduits conecting with said delivery pair of conduits in said delivery position, one of said aspirator pair of passages for receiving the sample fluid, a second of said outer members having a passageway connecting with said aspirator pair of conduits in said aspirator position and connecting with said delivery pair of conduits in said delivery position.

21. The transfer valve of claim 20 wherein each of said outer members has another passage connecting with one of said aspirator conduits in said delivery position.

22. An automatic dilution system for simultaneously diluting separate segments of a sample fluid comprising:

a transfer valve having a central member having at least a pair of conduits, a pair of outer membrs engaged against opposite faces of said central member, means for moving both of said outer members in opposite directions relative to said central member between a first and a second position, at least one of said outer members having at least one passageway connecting said pair of conduits in said first position, the other of said outer members having at least a pair of passages each connecting with a different one of said conduits in said first position, said passage, passageway and conduits forming a path through said valve for capturing separate sample segments along separate parts of said path, means for delivering sample fluid to said path, means for delivering diluent to said valve and to dilute the separate sample segments, and means for delivering the diluted separate sample segments from said valve to processing apparatus.

23. The dilution system of claim 22 wherein said one of said outer members has a pair of passages each communicating with a separate sample segment processing path of said delivering means and in said second position connecting with a different one of said conduits to deliver a sample segment to the associated processing path.

24. The dilution system of claim 23 wherein said conduits contain different volumes.

25. The dilution system of claim 22 wherein said central member has a second pair of conduits and each of said outer members has another passage connecting in said second position with the same conduit of the first pair of conduits whereby one sample segment is delivered from said one conduit by a path through said other passages and another sample segment is delivered from said passageway by a path through the second pair of conduits and passages in said other outer member connecting with said second pair of conduits in said second position.

* * * * *